United States Patent [19]

Würminghausen et al.

[11] Patent Number: 4,855,473

[45] Date of Patent: Aug. 8, 1989

[54] PROCESS FOR THE PREPARATION OF ORGANOOXYCHLOROSILANES

[75] Inventors: Thomas Würminghausen, Leverkusen; Karl Schneider; Franz Saykowski, both of Cologne; Hans G. Fröhlen, Leverkusen, all of Fed. Rep. of Germany

[73] Assignee: Bayer Aktiengesellschaft, Leverkusen, Fed. Rep. of Germany

[21] Appl. No.: 47,963

[22] Filed: May 8, 1987

[30] Foreign Application Priority Data

May 27, 1986 [DE] Fed. Rep. of Germany ....... 3617729
May 27, 1986 [DE] Fed. Rep. of Germany ....... 3617719

[51] Int. Cl.$^4$ ................................................. C07F 7/18
[52] U.S. Cl. .................................................... 556/471
[58] Field of Search ......................................... 556/471

[56] References Cited

U.S. PATENT DOCUMENTS

| | | | |
|---|---|---|---|
| 2,566,956 | 9/1951 | Pedlow | 556/471 X |
| 3,008,975 | 11/1961 | Schubert | 556/471 X |
| 3,448,138 | 6/1969 | DeWit | 556/471 |
| 3,492,328 | 1/1970 | Kötzsch | 556/471 |
| 3,522,284 | 7/1970 | Kötzsch | 556/471 |
| 3,546,267 | 12/1970 | Ismaic | 556/471 |
| 3,651,117 | 3/1972 | Bennett | 556/471 X |
| 4,111,974 | 9/1978 | Mazour et al. | 556/471 X |

FOREIGN PATENT DOCUMENTS

| | | | |
|---|---|---|---|
| 1419143 | 12/1963 | France | 556/471 |
| 2067636 | 8/1971 | France | 556/471 |
| 2273812 | 6/1974 | France | 556/471 |

OTHER PUBLICATIONS

Monatshefte für Chemie, vol. 95, 1964–pp. 1095–1098, Chem. Absts. vol. 100, Jan. 30, 1984.

*Primary Examiner*—Paul F. Shaver
*Attorney, Agent, or Firm*—Sprung Horn Kramer & Woods

[57] ABSTRACT

The present invention relates to the preparation of organooxychlorosilanes. They are produced by reacting the corresponding chlorosilane with an alcohol in the presence of a catalyst system consisting of hydrogen chloride and a cocatalyst.

2 Claims, No Drawings

PROCESS FOR THE PREPARATION OF ORGANOOXYCHLOROSILANES

The present invention relates to the preparation of organooxychlorosilanes. They are prepared by reacting the corresponding chlorosilane with alcohol in the presence of a catalyst system consisting of HCl and a cocatalyst.

The preparation of organo-organooxychlorosilanes by reacting organochlorosilanes with alcohols in a corresponding stoichiometric ratio is known (U. Wannagat and P. Geymayer, Monatshefte für Chemie 95, 1096 (1964), German Patent Specification No. 2 065 407 or German Patent Specification No. 2 427 085). These processes have the disadvantage that, in addition to the required product, undesired quantities of silanes having a different alkoxy/chlorine ratio are also obtained, which make it necessary to carry out an additional purification step and which reduce the yield.

Surprisingly it has now been found that the undesired quantities of silane by-products can be reduced with the aid of a catalyst system consisting of the hydrogen chloride produced during the reaction and a cocatalyst. Acid or basic components such as sulphonic acids, sulphuric acid or amines are suitable cocatalysts.

It was also surprising that the cleavage of alkyl chloride leading to the formation of undesired by-products was not observed (cf. W. Noll, Chemie und Technologie der Silicone (Chemistry and Technology of the Silicones), Verlag Chemie GmbH, Weinheim BergstraBe, 2nd edition 1968, page 72).

The success of the process of preparation according to the invention is even more surprising since, for example, the use of molar quantities of amines in the preparation of alkoxychlorosilanes has been described (German Patent Specification No. 2 065 407 and German Patent Specification No. 2 427 085) without any advantageous effect on the product composition having been observed.

The present invention relates to a process for the preparation of silanes of the general formula

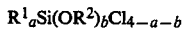

wherein

R$^1$ and R$^2$ independently of one another represent an alkyl, haloalkyl or alkenyl radical with 1 to 4 C atoms or an optionally substituted aromatic radical with 6 to 8 C atoms and a can be 0, 1 or 2 and b can be 4−a−1, by creating organochlorosilanes or SiCl$_4$ with compounds of the formula

wherein

R$^2$ has the abovementioned meaning, characterised in that the reaction is carried out in the presence of a catalyst system consisting of the hydrogen chloride formed during the reaction and a cocatalyst.

The silanes CH$_3$SiCl$_3$, C$_2$H$_5$SiCl$_3$, CH$_2$=CHSiCl$_3$, ClCH$_2$SiCl$_3$, C$_4$H$_9$SiCl$_3$, C$_6$H$_5$SiCl$_3$, (CH$_3$)$_2$SiCl$_2$ or SiCl$_4$ are, for example, suitable chlorosilanes.

The alcohols CH$_3$OH, C$_2$H$_5$OH, i-C$_3$H$_7$OH, n-C$_4$H$_9$OH, i-C$_4$H$_9$OH, CH$_3$OC$_2$H$_4$OH are examples of the compounds R$^2$OH which are used in the preparation according to the invention.

Suitable cocatalytically acting amines are primary, secondary or tertiary amines which can also be linked to form cycles by ring formation, such as, for example, 1,5-diazabicyclo(5.4.0)-undec-5-ene and aromatic amines. Triethylamine is the preferred amine. In view of the reaction to be expected between the added amine and hydrogen chloride and aminohydrochloride could of course also be added accordingly.

Possible acid cocatalysts are for example FSO$_3$H, ClSO$_3$H and CF$_3$SO$_3$H, C$_4$F$_9$SO$_3$H or C$_8$F$_{17}$SO$_3$H and H$_2$SO$_4$. The sulphonic acids, in particular perfluorobutanesulphonic acid, are particularly suitable.

The cocatalysts are preferably used in quantities of lower than a fifth molar part, based on the chlorosilane used. A tenth to a thousandth molar part is particularly preferred.

Since the stated sulphonic acids, the sulphuric acid or the amines or their hydrochlorides are only rapidly effective in respect of a favourable product distribution when hydrogen chloride is present, reaction temperatures of between −30° C. and +20° C., at which the hydrogen chloride formed is readily soluble in the reaction mixture, are advantageous for carrying out the process. Temperatures of below 15° C. are preferred. When higher temperatures are used the reaction must, if necessary, be carried out under pressure.

In the process according to the invention it is found to be advantageous if the cocatalyst used retains its activity in the distillation bottom products after the organooxychlorosilane to be prepared has been separated off by distillation and if it does not have to be readded when fresh chlorosilane and alcohol are metered in.

When appropriate quantities of the starting materials are used a process variant in which an organochlorosilane or SiCl$_4$ is symproportionated with an alkoxysilane with the aid of HCl and one of the stated cocatalysts, can also be carried out.

The molar ratio of chlorosilane to alcohol is based on the composition of the required product. It is possible to shift the equilibrium by using an excess of one of the reactants. Silanes which have been separated off by distillation can be recycled.

The organooxychlorosilanes prepared according to the invention are suitable starting products for the preparation of silanes which contain other functional groups in addition to alkoxy or, optionally, alkyl radicals. Examples of such groups are the amino, amido, oximino and acetoxy group. The stated silanes can be used in the production of room-temperature-curing silicone compositions.

The invention is illustrated in more detail by means of the following examples.

EXAMPLE 1 (COMPARISON EXAMPLE)

110 g=0.74 mol of methyltrichlorosilane were initially introduced at 20° C. into a three-necked flask (250 ml) equipped with a stirrer, a thermometer, a reflux condenser and a dropping funnel, which was protected against the entry of atmospheric moisture, and 30 g=0.65 mol of ethanol (molar ratio of methyltrichlorosilane:ethanol: 1.12:1) were added in the course of 5 minutes, with stirring. Hydrogen chloride was evolved vigorously and the temperature dropped to −5° C. When the addition had ended the mixture was heated until it boiled under reflux (ca. 90° C.). After 2 minutes the mixture was cooled and the reaction product was subjected to analysis by gas chromatography.

| Result: | $CH_3SiCl_3$ | 27.6% |
|---|---|---|
| | $CH_3Si(OC_2H_5)Cl_2$ | 39.3% |
| | $CH_3Si(OC_2H_5)_2Cl$ | 31.5% |

EXAMPLE 2

825 g (5.5 mols) of methyltrichlorosilane, 10.1 g (0.1 mol) of triethylamine and 230 g (5 mols) of ethanol were reacted.

The gas chromatogram gave the following product composition (in percent):

| Hours after beginning of reaction | $CH_3SiCl_3$ | $CH_3Si(OC_2H_5)Cl_2$ | $CH_3Si(OC_2H_5)_2Cl$ |
|---|---|---|---|
| 4 | 11.2 | 82.0 | 5.8 |
| 6 | 11.6 | 82.0 | 5.2 |
| 21 | 11.2 | 82.0 | 5.5 |

Then the product was heated to the boiling temperature, during which no formation of ethyl chloride was observed, and the composition changed only slightly compared with the analyses by gas chromatography.

EXAMPLE 3

Example 2 was repeated, but with the modification that only 0.01 or 0.001 mol of triethylamine were used instead of 0.1 mol of triethylamine. The following product composition was then recorded: 0.01/0.001 mol of triethylamine

| Hours after beginning of reaction | $CH_3SiCl_3$ | $CH_3Si(OC_2H_5)Cl_2$ | $CH_3Si(OC_2H_5)_2Cl$ |
|---|---|---|---|
| 4 | 20.8/28.1 | 58.3/43.6 | 20.2/27.6 |
| 6 | 14.8/— | 72.2/— | 12.3/— |
| 8 | 11.8/22.2 | 78.4/56.3 | 9.2/20.8 |
| 24 | 11.6/15.9 | 79.5/71.1 | 8.3/12.3 |

EXAMPLE 4

The experiment according to Example 2 was repeated, but with the modification that, instead of triethylamine, the bases diazabicycloundecene (0.001 mol) and 4-dimethylaminopyridine (0.001 mol) were used in each case. For comparison purposes ammonium chloride (0.5 mol) was used. The gas chromatograms gave the following percentages for each compound:

| Hours after beginning of reaction ( ) | $CH_3SiCl_3$ | $CH_3Si(OC_2H_5)Cl_2$ | $CH_3Si(OC_2H_5)_2Cl$ |
|---|---|---|---|
| Added compounds: | | | |
| Diazabicycloundecane (30) | 9.9 | 84.2 | 5.6 |
| 4-dimethylaminopyridine (24) | 10.3 | 80.9 | 7.3 |
| ammoniumchloride (20) | 28.8 | 41.6 | 28.7 |

EXAMPLE 5

Under the same conditions as described in Example 1 but in the presence of 1.8 g of $C_4F_9SO_3H$, the following result was obtained:

| $CH_3SiCl_3$ | 17.8% |
|---|---|
| $CH_3Si(OC_2H_5)Cl_2$ | 63.1% |
| $CH_3Si(OC_2H_5)_2Cl$ | 17.7% |

EXAMPLE 6

The influence of a prolonged residence time at between $-5°$ C. and $0°$ C. (2 hours) is shown by the following result (starting materials as in Example 5, using perfluorobutanesulphonic acid):

| $CH_3SiCl_3$ | 10.0% |
|---|---|
| $CH_3Si(OC_2H_5)Cl_2$ | 82.2% |
| $CH_3Si(OC_2H_5)_2Cl$ | 6.5% |

EXAMPLE 7

The influence of an increase in the molar excess of methyltrichlorosilane to 50% (starting materials: 225 g of $CH_3SiCl_3$, 46 g of ethanol, 1.8 g of perfluorobutanesulphonic acid), with a residence time of 3 hours at $0°$ C., is shown by the following result:

| $CH_3SiCl_3$ | 33.2% |
|---|---|
| $CH_3Si(OC_2H_5)Cl_2$ | 64.5% |
| $CH_3Si(OC_2H_5)_2Cl$ | 1.3% |

EXAMPLE 8

The reaction of methyltrichlorosilane and ethanol in a molar ratio of 1:1 (molar proportions) with 1 ml of sulphuric acid, with a residence time of 3 hours at $0°$ C., gives the following result:

| $CH_3SiCl_3$ | 9.2% |
|---|---|
| $CH_3Si(OC_2H_5)Cl_2$ | 78.4% |
| $CH_3Si(OC_2H_5)_2Cl$ | 9.0% |

EXAMPLE 9

The following result was obtained using the same method as in Example 8 but 1 ml of $HSO_3Cl$ as the catalyst:

| $CH_3SiCl_3$ | 6.1% |
|---|---|
| $CH_3Si(OC_2H_5)Cl_2$ | 81.4% |
| $CH_3Si(OC_2H_5)_2Cl$ | 9.9% |

EXAMPLE 10

37.5 g of methyltrichlorosilane (0.25 mol), 18.5 g of n-butanol (0.25 mol) and 0.5 ml of $C_4F_9SO_3H$ were used in a similar apparatus to that used in Example 1 but on a reduced scale (100 ml reactor), and the mixture was kept at $10°$ C. for 1 hour. Result (numbers in parentheses = result of the non-catalysed batch):

| $CH_3SiCl_3$ | 4.5% (7.0%) |
|---|---|

-continued

| | | |
|---|---|---|
| $CH_3Si(OC_4H_9)Cl_2$ | 77.3% | (64.4%) |
| $CH_3Si(OC_4H_9)_2Cl$ | 15.7% | (26.1%) |

EXAMPLE 11

149.5 g (1.0 mol) of methyltrichlorosilane and 32 g (1.0 mol) of methanol were reacted in the presence of 1 ml of chlorosulphuric acid in an apparatus according to Example 1. Then the mixture was kept at 0° C. for 3 hours. Result (values in parentheses=result of the non-catalysed batch):

| | | |
|---|---|---|
| $CH_3SiCl_3$ | 4.35% | (23.0%) |
| $CH_3Si(OCH_3)Cl_2$ | 79.6% | (47.0%) |
| $CH_3Si(OCH_3)_2Cl$ | 15.2% | (28.5%) |

EXAMPLE 12

72.36 kg (0.484 kmol) of methyltrichlorosilane and 0.463 kg of chlorosulphonic acid were initially introduced into a 250 ml enamel stirred kettle equipped with a heating (cooling) jacket, temperature measurement, a reflux condenser and an absorber for hydrogen chloride. 20.27 kg (0.44 kmol) of ethanol were metered in below the surface of the liquid at 11° to 12° C. in the course of 5 hours. When, after the addition of ethanol had ended, the reaction mixture had been stirred for a further 2 hours at the same temperature, it was heated to 70° C. in the course of 2 hours.

Analysis by gas chromatography gave the following result:

| | |
|---|---|
| $CH_3SiCl_3$ | 8.9% |
| $CH_3Si(OC_2H_5)Cl_2$ | 82.0% |
| $CH_3Si(OC_2H_5)_2Cl$ | 6.3% |

72.0 kg of $CH_3Si(OC_2H_5)Cl_2$ (boiling point 101° C.) were isolated by distillation.

EXAMPLE 13

An experiment was carried out following the same method as in Example 2, but with the modification that, instead of methyltrichlorosilane, 810 g of chloromethyltrichlorosilane (4.4 mols) and 185 g of ethanol (4.0 mols) were reacted; the gas chromatogram gave the following values:

| Hours after beginning of reaction | $ClCH_2SiCl_3$ | $ClCH_2Si(OC_2H_5)Cl_2$ | $ClCH_2Si(OC_2H_5)_2Cl$ |
|---|---|---|---|
| 4 | 9.5 | 77.5 | 7.8 |

EXAMPLE 14

868 g of phenyltrichlorosilane (4.1 mols) and 132 g of methanol (4.1 mols) were reacted, following the same procedure as in Example 2, either without or with the addition of 0.01 mol of triethylamine. The analysis by gas chromatography showed the following results for this step according to the invention and the comparison:

| Hours after beginning of reaction | $C_6H_5SiCl_3$ | $C_6H_5Si(OC_2H_5)Cl_2$ | $C_6H_5Si(OC_2H_5)_2Cl$ |
|---|---|---|---|
| without (4/30) | 29/27.3 | 32.6/33.1 | 33.0/34.5 |
| with (4/30) triethylamine | 7.1/4.9 | 79.0/80.1 | 11.5/10.2 |

EXAMPLE 15

52 g (0.85 mol) of tetraethoxysilane, 42.5 g (0.25 mol) of silicon tetrachloride and 0.5 ml of perfluorobutanesulphonic acid were mixed in an apparatus similar to that used in Example 1 and hydrogen choride was introduced until saturation was reached. The comparative experiment was carried out without perfluorobutanesulphonic acid and without hydrogen chloride.

| | $SiCl_4$ | $C_2H_5OSiCl_3$ | $(C_2H_5O)_2SiCl_2$ | $(C_2H_5O)_3SiCl$ | $(C_2H_5O)_4Si$ |
|---|---|---|---|---|---|
| without perfluorobutanesulphonic acid | 36.7 | 0.7 | 0.4 | 0.1 | 61.5 |
| with perfluorobutanesulphonic acid | 0.1 | 15.6 | 58.0 | 25.1 | 0.2 |

EXAMPLE 16

The reaction of silicon tetrachloride with methanol in a molar ratio of 1:1 was carried out at room temperature with and without the addition of 0.05 mol of triethylamine per mol of $SiCl_4$. The following gas chromatograms were obtained:

| | $SiCl_4$ | $CH_3OSiCl_3$ | $(CH_3O)_2SiCl_2$ | $(CH_3O)_3SiCl$ |
|---|---|---|---|---|
| without triethylamine | 31.8 | 34.8 | 13.6 | 19.2 |
| with triethylamine | 8.6 | 65.5 | 25.5 | 0.2 |

EXAMPLE 17

43 g (0.33 mol) of dimethyldichlorosilane and 15.3 g (0.33 mol) of ethanol were brought to reaction at 0° C. in the course of 5 minutes in the presence of 0.5 ml of perfluorobutanesulphonic acid. The gas chromatogram gave the following product composition in percent:

| | |
|---|---|
| $(CH_3)_2SiCl_2$ | 4.0 |
| $(CH_3)_2Si(OC_2H_5)Cl$ | 85.1 |
| $(CH_3)_2Si(OC_2H_5)_2$ | 8.9 |

What is claimed is:

1. In a process for the production of a silane of the formula $$R^1Si(OR^2)Cl_2$$

wherein
R$^1$ and R$^2$ independently of one another represent an alkyl, haloalkyl or alkenyl radical with 1 to 4 C atoms or represent an aromatic radical with 6 to 8 C atoms; by reaction of an organochlorosilane with a compound of the formula $$R^2OH,$$

the improvement which comprises carrying out the reaction in the presence of a catalyst system consisting of hydrogen chloride resulting from the reaction and a co-catalyst.

2. A process according to claim 1, wherein the cocatalyst is selected from the group consisting of primary, secondary or tertiary amines or sulphonic acids.

* * * * *

UNITED STATES PATENT AND TRADEMARK OFFICE
CERTIFICATE OF CORRECTION

PATENT NO.  : 4,855,473

DATED       : August 8, 1989

INVENTOR(S) : Wurminghausen et al.

It is certified that error appears in the above-identified patent and that said Letters Patent is hereby corrected as shown below:

| | |
|---|---|
| Title Page | U.S. PATENT DOCUMENTS: After " 3,546,267, 12/1970 " delete " Ismaic " and substitute -- Ismail -- OTHER PUBLICATIONS: After " 1984" add -- Bazant et al; "organasilicon compounds, " Vol. 1 academie oreas (NY) 1965. pp 51. -- |
| Col. 2, line 37 | Delete " organochlorosilane " and substitute -- organooxychlorosilane -- |
| Col. 8, line 12 | After " reaction " add -- in liquid state with approximately equimolar amounts of organochlorosilane and alkanol -- |
| Col. 8, line 17 | After " acids. " add -- , and $R^2$ represents an alkyl. haloalkyl or alkenyl radical with 1 to 4 C atoms. -- |

Signed and Sealed this

Twenty-ninth Day of January, 1991

*Attest:*

HARRY F. MANBECK, JR.

*Attesting Officer*   *Commissioner of Patents and Trademarks*